United States Patent [19]
Nakatsu et al.

[11] Patent Number: 5,466,718

[45] Date of Patent: Nov. 14, 1995

[54] TYROSINASE INHIBITORS

[75] Inventors: Tetsuo Nakatsu, Walnut Creek; Kok Lean R. Kang, Oakland; Kelly L. McAlister; Jiansheng Huang, both Conrad, all of Calif.

[73] Assignee: Takasago Institute for Interdisciplinary, Walnut Creek, Calif.

[21] Appl. No.: 41,771

[22] Filed: Apr. 2, 1993

[51] Int. Cl.⁶ .................. A61K 31/045; A61K 31/01; A61K 31/19

[52] U.S. Cl. .................. 514/724; 514/557; 514/762; 514/947

[58] Field of Search .................. 514/526, 546, 514/724, 762, 947, 557

[56] References Cited

U.S. PATENT DOCUMENTS 4,052,515  10/1977  McDermott et al. .................. 514/724
4,853,413  8/1989  Katz et al. .................. 514/724

FOREIGN PATENT DOCUMENTS 52-122637  10/1977  Japan .

OTHER PUBLICATIONS

*The Merck, Index*, 10th Ed. (1983) p. 332, abstract No. 2302.
CA (13:29295n) 1989.
Chemical Abstracts 113(4):29294m 1989.

Primary Examiner—Raymond Henley, III
Assistant Examiner—K. Weddington
Attorney, Agent, or Firm—Fish & Richardson

[57]  ABSTRACT

Methods and compositions are provided for inhibiting the activity of tyrosinase in a host and, as a result, inhibiting melanin-formation. The tyrosinase-inhibitor active ingredient is a compound or mixture of compounds represented by the following structural formulae (I) and (II):

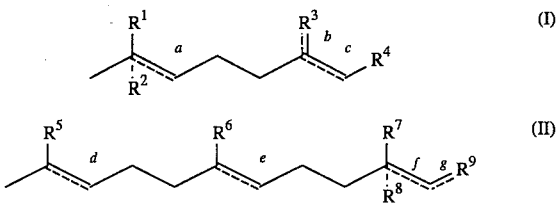

wherein the dotted lines at a, b, c, d, e, f, g, represent an optional double bond, provided that double bonds are not at both b and c, or at both f and g, at the same time; $R^1$, $R^5$, $R^6$, and $R^7$ are each hydrogen or methyl; $R^2$ and $R^8$ are each no group, or each hydrogen or hydroxyl when there is no double bond at a and at f, respectively; $R^3$ is methylene when there is a double bond at b, or hydrogen or methyl when there is no double bond at b; $R^4$ is formyl or $-(CH_2)_n-R^{10}$, wherein $R^{10}$ is hydrogen, hydroxyl, acyloxy, or cyano and n is an integer of from 1 to 3; and $R^9$ is methylene when there is a double bond at g, or $-(CH_2)_n-R^{10}$ when there is no double bond at g.

8 Claims, No Drawings

TYROSINASE INHIBITORS

BACKGROUND OF THE INVENTION

1. Field of the Invention

This invention relates generally to acyclic terpenoid compounds such as citronellol, geraniol and their derivatives which possess tyrosinase inhibitory, melanin-formation inhibitory, and skin whitening activities.

2. Description of Related Art

Skin pigmentation and tanning are related to the amount of melanin in epidermal melanosomes. In the melanosomes, tyrosine is oxidized to dopa and dopaquinone by the enzyme tyrosinase; the resulting intermediate compounds polymerize to form the brown-black melanin pigment. The formation of melanin is believed to be a defensive mechanism in humans which protects their skin from harmful ultraviolet rays. However, the excessive formation of melanin following prolonged sun exposure or due to disorders of epidermal melanin units is responsible for melasma, ephelides, and pigmented cosmetic dermatitis.

Although the precise mechanism of excessive melanin formation has not been fully elucidated, the activation of tyrosinase appears to be a significant factor. Thus, the development of chemical agents capable of modulating the enzyme activity of tyrosinase would have considerable value for the control of the above-noted undesirable skin conditions.

Some tyrosinase inhibitors are known already. These inhibitors include lipoic acids, thiopronions, glutathiuones, pantetheines, flavonols, hydroquinones, pyrones, and kojic acids. Among them, arbutin, one of the hydroquinones, has been used widely. Illustrative references directed to such tyrosinase inhibitors follow.

Japan Kokai 1-305,025, 1-305,026, 2-193,917, and 2-193,918 disclose alkanoic acids, the esters thereof, and unsaturated fatty acids for inhibition of biosynthesis of tyrosinase. Japan Kokai 3-109,319 discloses 5-farnesyl-6-methylresorcinol (neogrifolin) that is a tyrosinase inhibitor.

There has been a need for tyrosinase inhibitors capable of effectively inhibiting the activity of tyrosine and which could be used on a long term basis without undesirable side effects on the human skin. In spite of research activities, up to now, no one has recognized that certain acyclic terpenoid compounds or the derivatives thereof could inhibit tyrosinase or melanin formation. Accordingly, this invention provides methods for inhibiting tyrosinase or melanin formation in living cells. Such methods desirably include topical treatment of humans with a composition containing the acyclic terpenoid compounds.

SUMMARY OF THE INVENTION

In accordance with the present invention, certain acyclic terpenoid compounds and their derivatives are provided, which are potent inhibitors of tyrosinase. Specifically, the invention employs compounds of formula (I) or formula (ii):

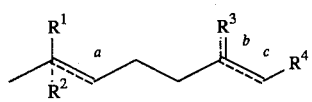

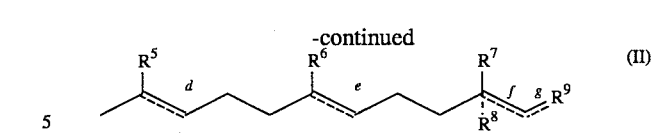

wherein the dotted lines at a, b, c, d, e, f, g, represent an optional double bond, provided that double bonds are not present at both b and c, or at both f and g, at the same time; $R^1$, $R^5$, $R^6$, and $R^7$ are each hydrogen or methyl; $R^2$ and $R^8$ are each no group, or each hydrogen or hydroxyl when there is no double bond at a and at f, respectively; $R^3$ is methylene when there is a double bond at b, or hydrogen or methyl when there is no double bond at b; $R^4$ is formyl or $-(CH_2)_n-R^{10}$, wherein $R^{10}$ is hydrogen, hydroxyl, acyloxy, or cyano and n is an integer of from 1 to 3; and $R^9$ is methylene when there is a double bond at g, or $-(CH_2)_n-R^{10}$ when there is no double bond at g.

The present invention also provides a pharmaceutical composition comprising a compound of formula (I) or a compound of formula (II), together with a pharmaceutically acceptable carrier.

The present invention further provides a method for inhibiting melanin-formation in a host, which comprises administering to the host an inhibitory effective amount of at least one compound selected from the group consisting of compounds of formula (I) and compounds of formula (II).

The present invention still further provides a method for inhibiting tyrosinase in a host, which comprises administering to the host an inhibitory effective amount of at least one compound selected from the group consisting of compounds of formula (I) and compounds of formula (II).

DETAILED DESCRIPTION OF THE INVENTION

Some of the compounds of formula (I) or formula (II) are naturally occurring terpenoids. Preferred individual natural compounds of formula (I) or formula (II) are provided below:

Citronellol: a compound of formula (I) wherein a is a double bond; b and c are both a single bond; $R^1$ is methyl; $R^3$ is methyl; and $R^4$ is $CH_2OH$.

Geraniol a compound of formula (I) wherein a and c are both a double bond; b is a single bond; $R^1$ is methyl; $R^3$ is methyl; and $R^4$ is $CH_2OH$ in a trans form.

Nerol: a compound of formula (I) wherein a and c are both a double bond; b is a single bond; $R^1$ is methyl; $R^3$ is methyl; and $R^4$ is $CH_2OH$ in a cis form.

3,7-Dimethyloctanol: a compound of formula (I) wherein a, b, and c are each single bond; $R^1$ is methyl; $R^2$ is hydrogen; $R^3$ is methyl; and $R^4$ is $CH_2OH$.

Hydroxycitronellol: a compound of formula (I) wherein a, b, and c are each single bond; $R^1$ is methyl; $R^2$ is hydroxyl; $R^3$ is methyl; and $R^4$ is $CH_2OH$.

Dihydromyrcenol: a compound of formula (I) wherein a is a single bond; b is a double bond; $R^1$ is methyl; $R^2$ is hydroxyl; $R^3$ is methylene; and $R^4$ is methyl.

Farnesol: a compound of formula (II) wherein d, e, and f are each a double bond; $R^5$ is methyl; $R^6$ is methyl; $R^7$ is methyl; and $R^9$ is $CH_2OH$.

Nerolidol: a compound of formula (II) wherein d, e, and f are each a double bond; $R^5$ is methyl; $R^6$ is methyl; $R^7$ is methyl; $R^8$ is hydroxyl; and $R^9$ is $CH_2OH$.

A preferred group of compounds of formula (I) are those wherein $R^4$ is represented by formula $(CH_2)_n-R^{10}$ wherein $R^{10}$ is hydroxyl. Within this group, particularly preferred compounds are octanol and decanol.

A second preferred group of compounds of formula (I) are those wherein $R^4$ is formyl. Within this group, particularly preferred compounds are citronellal, geranial, neral, hydroxycitronellal, octyl aldehyde, and decyl aldehyde.

A third preferred group of compounds of formula (I) are those wherein $R^4$ is represented by formula $(CH_2)_n$—$R^{10}$ wherein $R^{10}$ is acyloxy.

A fourth preferred group of compounds of formula (II) are those wherein $R^9$ is $(CH_2)_n$—$R^{10}$ wherein $R^{10}$ is acyloxy.

As used herein, the "acyloxy" group may contain straight- or branched-chain alkyl with 1–4 carbon atoms or aromatic acyl group.

Within the third and fourth preferred groups, especially preferred compounds are citronellyl formate, citronellyl acetate, citronellyl propionate, citronellyl butyrate, citronellyl isobutyrate, citronellyl benzoate, citronellyl phenylacetate, geranyl formate, geranyl acetate, geranyl propionate, geranyl butyrate, geranyl isobutyrate, geranyl isovalerate, geranyl benzoate, geranyl phenylacetate, farnesyl formate, farnesyl acetate, farnesyl propionate, farnesyl butyrate, farnesyl isobutyrate, farnesyl benzoate, and farnesyl phenylacetate.

A fifth preferred group of compounds of formula (I) are those wherein $IR^4$ is represented by formula $(CH_2)_n$—$R^{10}$ wherein $R^{10}$ is cyano.

A sixth preferred group of compounds of formula (II) are those wherein $R^9$ is $(CH_2)_n$—$R^{10}$ wherein $R^{10}$ is cyano.

Within the fifth and sixth preferred groups, especially preferred compounds are citronellylnitrile and geranylnitrile.

The compounds of formulae (I) and (II) have ability to inhibit tyrosinase. As used herein, "inhibitory effective amount" or "effective amount" of the active compound means an amount sufficient to result in 40–100% inhibition of the enzyme tyrosinase, as determined by an in vitro assay.

As used herein, the term "host" includes humans and non-human mammals. By non-human mammals, is meant domestic animals such as dogs, cats, and horses.

Compounds of formula (I) wherein $R^4$ is hydroxyl and compounds of formula (V) wherein $R^9$ is —$(CH_2)_n$—$R^{10}$ wherein $R^{10}$ is hydroxyl can form pharmaceutically acceptable alkoxides. These derived alkoxides possess the same activity as the parent alcohols and are included within the scope of this invention. Suitable alkoxides include those of alkali metals or alkali earth metals such as sodium, potassium, magnesium and calcium.

Among the above-enumerated compounds, citronellol, geraniol, farnesol, and the esters of the foregoing derived from straight- or branched-chain acyclic carboxylic acids having 1 to 4 carbon atoms or from benzoic acid are particularly preferred because of their high tyrosinase inhibitory activities as well as high melanin pigment-formation inhibitory action. Especially preferred compounds are citronellyl butyrate, geranyl butyrate, and farnesyl butyrate, since they are considered safe to a host.

It has been found that application of topical compositions containing the compounds of the present invention are useful to improve or heal a variety of deleterious skin conditions related to the formation and accumulation of melanin. For example, these compounds can be used to prevent the formation of melasma, ephelides, and sunburn as well as to treat pigmented cosmetic dermatitis. Some of the above-enumerated compounds have been used as flavoring agents, and fragrances, and are readily available from natural sources or by synthesis. See S. Arctander, Perfume and Flavor Chemicals: Montclair, 1961; and G. Indo, "Koryo no Jissai Chishiki" (in the Japanese language): Toyo Keizai Shimpo Co., Ltd., 1975.

The compounds of this invention contain asymmetric carbons. Thus, these compounds can exist as an optically active form. The present invention embraces both optically active compounds and optically inactive compounds. One or more compounds of this invention can be co-applied to the skin of a host in a single formulation. Alternatively, they can be applied concurrently as separate formulations. Still further, one compound can be applied before or after application of the other compounds provided that the time interval between the two (or more) is not lengthy. It is, however, preferred to use these compounds as a single composition or formulation. For example, citral which can be obtained from natural lemon grass oil is a mixture of neral and geraniol. Thus, citral can be used as it is supplied.

The compounds of this invention will typically be presented in a pharmaceutically acceptable carrier for application to the affected area. The nature of the carriers may vary widely and can be adapted to the intended location or duration of application. Creams, gels, lotions, ointments, suspensions, emulsions, and packs are all suitable. Suitable carriers include water, organic solvents such as lower alcohols (ethanol, isopropyl alcohol, etc.) and acetone. A cream or ointment base also finds use and is frequently preferable. Suitable bases include lanolin, polyethylene glycol, and liquid paraffin. The compounds of this invention may be included in white wax or white vaseline.

Additional ingredients may be added to the composition of this invention, as long as they are pharmaceutically acceptable and not deleterious to the skin. Examples of ingredients which can be added to the composition include stabilizers, preservatives, buffering agents, antioxidants, deodorizing agents, binding agents, additional fragrances, pigments, and the like.

The compounds of this invention are also administered orally or parenterally in admixture with conventional pharmaceutical carriers. They may, if desired, also be administered in appropriate pharmaceutically acceptable carriers, intravenously, subcutaneously, intramuscularly and intracutaneously. For oral administration, they may be administered in such forms as tablets, dispersible powders, granules, capsules, syrups and elixirs.

The concentration of the compounds of this invention in the composition is not critical as long as sufficient active material is present to provide demonstratable effects. Usually the active compound will be present in a composition at from at least about 0.001 to about 5.0% by weight, more preferably from about 0.05 to about 1.0% by weight.

Although the compositions and methods are most commonly used with humans and the treatment of human skin, treatment of skin of other mammals is also contemplated.

As indicated earlier, the active compounds of this invention have been safely used as flavoring agents, fragrances, and base materials for cosmetics and medicaments, and their low toxicity has been recognized by those skilled in the art. The in vivo cytotoxity tests were conducted on representative terpenoids in animals and compiled in the data sheets provided by Aldrich Company, the disclosure of which is incorporated by reference.

Without further elaboration, it is believed that those skilled in the art can, using the preceding description, utilize the present invention to its fullest extent. The following examples are, therefore, to be construed as merely illustrative and not a limitation of the scope of the present invention in any way.

MATERIALS

Citronellol, geraniol, farnesol, nerolidol, dihydromyrcenol, citronellal, citral, octanol, decanol and arbutin were available from Sigma Chemical Co. (St. Louis, Mo.). Citronellyl formate, citronellyl acetate, citronellyl propionate, citronellyl butyrate, and citronellylnitrile were available from Takasago International (Tokyo, Japan). Other chemicals used were synthesized by the methods described below, and their chemical structures were determined by spectroscopy, and all the starting substances used for the syntheses were obtained from Sigma Chemical Co., Aldrich Chemical Company (Milwaukee, Wis.), Pfaltz and Bauer AG (Waterbury, Conn.), or Takasago International Corporation (Tokyo, Japan).

EXAMPLE 1

TYROSINASE INHIBITION

The active compounds used in the present invention and a control compound (arbutin) were tested for their 50% enzyme (tyrosinase) activity inhibition concentration ($IC_{50}$) by the following method, and results obtained are shown in Table 2 below.

Inhibition tests were carried out using aqueous solvents. Saturated stock solutions were prepared by at least 48 hours before the tests were run, which were diluted appropriately upon use in order to increase the solubilities in the aqueous solvents of the lipophilic test compounds.

Tests were carried out according to conventional procedure as follows. That is, 0.01 to 0.02 ml of a mushroom tyrosinase solution (1,375 U/ml, Sigma Chemical Co.), 0.98 to 0.99 ml of a 0.07M phosphate buffer solution (pH 6.8) and 1 ml of a test solution with or without a test compound listed in Table 2 were mixed, and the resulting mixture was incubated at 22° C. for 8 minutes. Then, 1 ml of a 0.03% aqueous solution of I-DOPA (L-3,4-dihydroxyphenylalanine having a purity of 99%, Sigma Chemical Co.) was added thereto. After incubation at 22° C. for 2 minutes, the amount of dopachrome in the reaction mixture was measured as absorbance (optical density) at 475 nm. The change in absorbance with or without different test samples was monitored every 30 seconds for the following 2.5 minutes using a Beckman DU-64 spectrophotometer (Beckman, Palo Alto, Calif.).

Each test compound was repeatedly tested until the 50% inhibitory concentration ($IC_{50}$) (µg/ml) was determined. If a compound showed 40 to 60% inhibition at a concentration for a minimum of two trials, this was determined as the $IC_{50}$ value.

The percent inhibition was calculated according to the following equation:

$$\% \text{ Inhibition} = \frac{\Delta A_{control} - \Delta A_{sample}}{\Delta A_{control}}$$

where
A=Absorbance
$\Delta A = A_{final} - A_{initial}$
$A_{final}$=Final absorbance
$A_{initial}$=Initial absorbance

TABLE 2

| Test Compound | $IC_{50}$ (µg/ml) |
| --- | --- |
| Citronellol | 6.3 |
| Citronellyl formate | 6.3 |
| Citronellyl acetate | 18.8 |
| Citronellyl propionate | 12.5 |
| Citronellyl isobutyrate | 6.3 |
| Citronellyl butyrate | 37.5 |
| Citronellyinitrile | 9.4 |

TABLE 2-continued

| Test Compound | $IC_{50}$ (µg/ml) |
| --- | --- |
| Citronellyl benzoate | 6.3 |
| Geraniol | 6.3 |
| Geranyl isobutyrate | 12.5 |
| Nerolidol | 12.5 |
| Dihydromyrcenol | 12.5 |
| Farnesol | 12.5 |
| Farnesyl isobutyrate | 12.5 |
| Farnesyl benzoate | 25.0 |
| Farnesyl phenylacetate | 12.5 |
| Citronellal | 9.4 |
| Octanol | 12.5 |
| Decanol | 12.5 |
| Arbutin | 63 |

Table 2 shows that the tested compounds had higher activity levels than arbutin, which is a known skin bleaching agent.

EXAMPLE 2

TYROSINASE INHIBITION (LONG EXPOSURE)

Tyrosinase inhibitory effects of the active compounds of this invention on long exposure were determined using tyrosinase as a substrate. Results are shown in Table 3.

The method of Chen et al. (J. Agric. Food Chem., 39, 8, 1991) was adapted and scaled down for spectrophotometric analysis on a Bio Rad Model 3550 Microplate Reader (Bio-Rad, Richmond, Calif.), which uses 96-well plates.

20 µl of tyrosinase solution containing 0.02 mg/ml of tyrosinase (Sigma Chemical Company) and 76 µl of a test solution of citronellol, geraniol, or farnesol, adjusted to 200 µg/ml with a phosphate buffer solution (pH 6.8) were added to each well. After incubation at 37° C. for 8 minutes, 1 mM L-tyrosine (Sigma Chemical Company) was added as a substrate. Absorbance at 490 nm was measured every 60 seconds for up to 120 minutes to determine how much the amount of melanin produced from tyrosine substrate decreased as a result of the tyrosinase inhibition.

TABLE 3

| Time (minute) | Inhibition Ratio (%) on Melanin Formation | | |
| --- | --- | --- | --- |
| | Citronellol | Geraniol | Farnesol |
| 0 | 0 | 0 | 0 |
| 30 | 39.6 | 37.3 | 23.6 |
| 120 | 43.8 | 48.5 | 31.9 |

Table 3 shows that the active compounds of this invention increases the inhibition ratio of melanin formation from a tyrosine substrate after 120 minutes of inoculation. These results demonstrate that the activity of tyrosinase which forms melanin is effectively inhibited by the active compounds of this invention over a long period.

EXAMPLE 4

MELANIN FORMATION INHIBITION

Inhibitory effects on the melanin formation in melanoma cells were tested by the following procedure. Results obtained are shown in Table 5, together with the results obtained with arbutin as a control.
Melanin Formation Assay Mouse melanoma cell line (ATCC CRL 6322) was maintained in MEM medium (GIBCO BR, Gaitherburg, Md.) supplemented with 10% heat-inactivated fetal bovine serum described by Maeda (J. Cosmet. Chem., 42, 361 (1991)). More specifically, the cells were cultured on 6-well tissue culture plates (Falcon 3046) with various concentrations of each test compound listed in Table 5 below at 37° C., and at a humidity of 98%, in 5% carbon dioxide atmosphere for 4 days. Cell viability in all tests was determined by Trypan Blue exclusion. The culture media were aspirated, and 1.0 ml of an aqueous 0.25% trypsin solution and an aqueous 0.2% ethylenediaminetetraacetic acid (EDTA) solution were added to each well. Detached cells were placed in an Eppendorf tube, and centrifuged at 1,000 rpm for 5 minutes. The cell pellets thus obtained were mixed with 5% trichloroacetic acid, agitated well, and centrifuged 10,000 rpm to deposit melanin. The melanin pellets were mixed with 1N NaOH for dissolution, and the absorbance at 475 nm was measured, from which melanin formation inhibition (%) was calculated.

TABLE 5

| Test Compound | Concentration (mM) | Inhibition (%) |
|---|---|---|
| Citronellol | 0.5 | 25 |
|  | 0.25 | 25 |
| Geraniol | 0.5 | 18 |
|  | 0.25 | 30 |
| Citronellyl isobutyrate | 0.5 | 56 |
|  | 0.25 | 31 |
| Arbutin | 0.25 | 53 |
|  | 0.125 | 58 |

Results in Table 5 show that the active compounds of this invention inhibit not only the activity of tyrosinase but also melanin formation in melanoma cells. Since the assay was performed in an aqueous system, the control compound, arbutin (which is hydrophilic) exhibited higher inhibitory effects than the active compounds of the present invention, which are lipophilic. However, the lipophilic compounds used in the present invention are more permeable to the skin and more effective to the human body than is arbutin.

EXAMPLE 5

LOTION FORMULATION

The following ingredients were blended in the following proportions by weight.

| Ingredient | w/w % |
|---|---|
| Part A: | |
| Mineral oil | 55% |
| Triton X-100 (trademark for p-t-octyl-phenoxypolyethoxyethanol, produced by Union Carbide Chemical and Plastic) | 2% |
| Part B: | |
| Triethanolamine | 1.5% |
| Glycerol | 3% |
| Citronellyl isobutyrate | 0.1% |
| Water | q.s |

Part A components were heated to 62° C. and Part B components to 65° C. The components of Part B were added to Part A components and the resulting mixture was cooled to room temperature under stirring to obtain a lotion.

EXAMPLE 6

ANTI-TYROSINASE TEST FOR LOTION

Tyrosinase (20 µl) was added to 5 ml of a test solution containing the lotion prepared in Example 5, and 100 µl of L-DOPA was added thereto. The test solution was stirred at room temperature. The enzyme activity as darkness of the lotion was measured after 3 hours using KODAK Gray Scale.

Sample 1 contained 1 mg/ml of citronellyl isobutyrate. Sample 2 was obtained by diluting Sample 1 by 10 folds.

Control 1 contained no active compound. Control 2 was obtained by diluting Control 1 by 10 folds.

Results obtained are shown in Table 6 below.

TABLE 6

| Lotion | Gray Scale |
|---|---|
| Sample 1 | 3 |
| Sample 2 | 3 |
| Control 1 | 11.5 |
| Control 2 | 11.5 |

Results in Table 5 revealed that the lotion of the present invention inhibited the activity of tyrosinase considerably.

EXAMPLE 7

CREAM FORMULATION

The following ingredients were blended in the following proportions by weight.

| Ingredient | w/w % |
|---|---|
| Citronellyl isobutyrate | 0.1% |
| Butanediol | 5.0% |
| Beeswax | 2.0% |
| Lanolin | 10.0% |
| Squalene | 30.0% |
| Polyoxyethylenesorbitan monolaurate | 2.0% |
| Water | q.s. |

EXAMPLE 8

SUNSCREEN GEL FORMULATION

The following ingredients were blended in the following proportions by weight.

| Ingredient | w/w % |
|---|---|
| Ethyl alcohol | 10.0% |
| 1,2-Propylene glycol | 10.0% |
| Germaben 11 (propylene glycol + diazolidinylurea + methyl p-hydroxybenzoate + propyl p-hydroxybenzoate, SUTTON, trademark for a product by Sutton Lab (NJ)) | 1.00% |
| Allantoin | 0.10% |
| D-Panthenol | 0.50% |
| Carboxypolymethylene | 1.10% |
| Triethanolamine | 2.20% |
| Citronellyl isobutyrate | 0.10% |
| Fragrances | 1.00% |
| Water | q.s. |

EXAMPLE 9

FACE POWDER

The following ingredients were blended in the following proportions by weight according to conventional procedure.

| Ingredient | w/w % |
|---|---|
| Titanium oxide | 7.0% |
| Zinc oxide | 57.0% |
| Talc | 19.0% |
| Zinc stearate | 10.8% |
| Starch | 5.0% |
| Citronellyl isobutyrate | 0.1% |
| Fragrances | 1.1% |

PREPARATION 1

SYNTHESIS OF GERANYL ISOBUTYRATE

A mixture of geraniol (355 mg, 2.3 mmol) and isobutyryl chloride (407 mg, 3.8 mmol) was refluxed for 4.5 hours in 9.5 ml of methylene chloride ($CH_2Cl_2$) and 2 ml of pyridine. After the reflux, the reaction mixture was quenched over ice/water, extracted with hexane, washed, and dried over magnesium sulfate. The reaction mixture was concentrated under vacuum at 32° C. to yield 161 mg of oil, which was then purified by open column chromatography using ethyl acetate/hexane (5/95) as an eluant to afford 119 mg (yield: 33%) of a pale yellow oil having the following physical properties.
MS:m/z 224 $[M^+]$ $^1$H NMR ($CDCl_3$, 500 MHz): δppm 5.32 (t,1H,J=6.6 Hz), 5.06 (t,1H,J=6.8 Hz), 4.57 (d,2H,J=6.8 Hz), 2.55–2.49 (m,1H), 2.10–2.01 (m,4H), 1.68 (bs,3H), 1.66 (bs,3H), 1.50 (s,3H), 1.14 (d,6H,J=7.1 Hz).

PREPARATION 2

SYNTHESIS OF FARNESYL ISOBUTYRATE

A mixture of farnesol (356 mg, 1.6 mmol) and isobutyryl chloride (407 mg, 3.8 mmol) was refluxed for 2 hours. Extraction with hexane, and purification yielded 35.9 mg (yield: 7.8%) of oil having the following physical properties.
MS:m/z 292 $[M^+]$ $^1$H NMR ($CDCl_3$, 500 MHz): δppm 5.33 (m,1H), 5.09 (m,2H), 4.57 (d,2H,J=7.3 Hz), 2.55–2.51 (m,1H), 2.11–1.96 (m,8H), 1.69 (bs,3H), 1.66 (bs, 3H), 1.58 (bs,3H), 1.14 (d,6H,J=6.8 Hz).

PREPARATION 3

SYNTHESIS Of FARNESYL BENZOATE

A mixture of farnesol (445 mg, 2 mmol) and benzyl chloride (605 mg, 4.3 mmol) was refluxed for 3 hours. Extraction with hexane, and purification yielded 391 mg (yield: 60%) of clear yellow oil having the following physical properties.
MS:m/z 326 $[M^+]$ $^1$H NMR ($CDCl_3$, 500 MHz): δppm 8.03 (bd,2H,J=8.0 Hz), 7.52 (m,1H), 7.40 (t,2H,J=8.0 Hz), 5.46 (dd,1H,J=12.8,8.1 Hz), 5.09 (m,2H), 4.83 (d,2H,J=7.3 Hz), 2.17–1.95 (m,8H), 1.66 (bs,3H), 1.59 (bs,3H), 1.57 (bs,3H), 1.51 (s,3H).

PREPARATION 4

SYNTHESIS Of FARNESYL PHENYLACETATE

A mixture of farnesol (440 mg, 2 mmol) and phenylacetyl chloride (584 mg, 7.8 mmol) was refluxed for 2.5 hours. Extraction with hexane, and purification yielded 368 mg (yield: 54%) of oil having the following physical properties.
MS:m/z 340 $[M^+]$ $^1$H NMR ($CDCl_3$, 500 MHz): δppm 7.31–7.22 (m,5H), 5.32 (m,1H), 5.08 (m,2H), 4.60 (d,2H, J=6.8 Hz), 3.60 (m,22H), 2.11–1.95 (m,8H), 1.66 (bs,6H), 1.58 (bs,3H), 1.50 (s,3H).

PREPARATION 5

SYNTHESIS OF CITRONELLOL BENZOATE

A mixture of benzoic acid (14.6 g, 0.12 mol) and citronellol (15.6 g, 0.1 mol) in tetrahydrofuran (THF) was heated on a water bath for 4 hours after the addition of concentrated sulfuric acid. The reaction was monitored by thin layer chromatography (TLC), and when the reaction was over, the reaction mixture was quenched over ice/water, extracted with THF or methylene chloride, washed with 5% sodium hydrogen carbonate, and dried over magnesium sulfate. The reaction mixture was concentrated under vacuum and purified by open column chromatography to yield 4.95 g (yield: 19%) of a product having the following physical properties.
MS:m/z 260 $[M^+]$ $^1$H NMR ($CDCl_3$, 500 MHz): δppm 8.02 (dd,2H,J=7.3,1.3 Hz), 7.53 (tt,1H,J=7.3,1.3 Hz), 7.41 (td, 2H,J=7.3,1.3 Hz), 5.09 (bt,1H), 4.35 (m,2H), 1.99 (m,2H), 1.66 (bs,3H), 1.59 (s,3H), 0.96 (d,J=6.84 Hz,3H).

PREPARATION 6

SYNTHESIS Of CITRONELLYL ISOBUTYRATE

A mixture of isobutyryl chloride (410 mg, 3.8 mmol) and citronellol (340 mg, 2.2 mmol) was refluxed for 2.5 hours. Extraction with hexane, and purification yielded 480 mg (yield: 96.6%) of an ester having the following physical properties.
MS:m/z 226 $[M^+]$ $^1$H NMR ($CDCl_3$, 500 MHz): δppm 5.07 (m,1H), 4.08 (m,2H), 2.51 (m,1H), 1.99 (m,2H), 1.66 (s,3H), 1.58 (s,3H), 1.14 (s,3H), 1.13 (s,3H), 0.90 (d,3H,J= 6.5 Hz).

What is claimed is:

1. A method for inhibiting melanin-formation in a host in need thereof, which comprises administering to the host an effective amount of at least one melanin-formation inhibiting compound selected from the group consisting of compounds of formula (I) and compounds of formula (II):

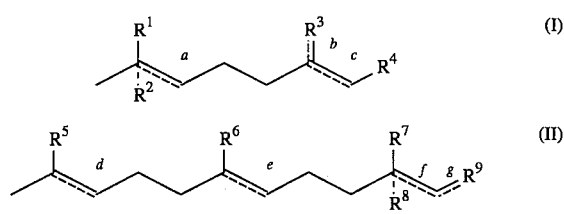

wherein the dotted lines at a, b, c, d, e, f, g, represent an optional double bond, provided that double bonds are not at both b and c, or at both f and g, at the same time; $R^1$, $R^5$, $R^6$, and $R^7$ are each hydrogen or methyl; $R^2$ and $R^8$ are each no group, Or each hydrogen or hydroxyl when there is no double bond at a and at f, respectively; $R^3$ is methylene when there is a double bond at b, or hydrogen or methyl when there is no double bond at b; $R^4$ is formyl or —$(CH_2)_n$—$R^{10}$, wherein $R^{10}$ is hydrogen, hydroxyl, acyloxy, or cyano and n is an integer of from 1 to 3; and $R^9$ is methylene when there is a double bond at g, or —$(CH_2)_n$—$R^{10}$ when there is no double bond at g.

2. The method according to claim 1, wherein the melanin-formation inhibiting compound is selected from the group consisting of citronellol, geraniol, farnesol, nerelidol, dihydromyrcenol, citronellol, octanol decanol, and the esters thereof derived from a carboxylic acid having one to four carbon atoms, or from benzoic acid.

3. The method according to claim 2, wherein the melanin-formation inhibiting compound is selected from the group consisting of citronellyl isobutyrate, geranyl isobutyrate, and farnesyl isobutyrate.

4. The method of claim 1, wherein the host has a melanin-formation disorder.

5. A method for inhibiting the activity of tyrosinase in a host in need thereof, which comprises administering to the host an effective amount of at least one tyrosinase-inhibiting compound selected from the group consisting of compounds of formula (I) and compounds of formula (II):

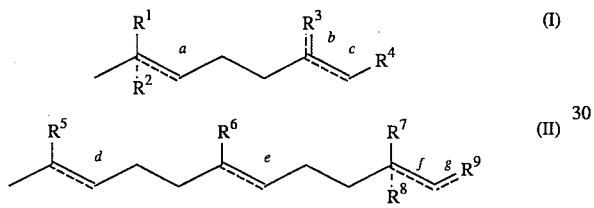

wherein the dotted lines at a, b, c, d, e, f, g, represent an optional double bond, provided that double bonds are not at both b and c, or at both f and g, at the same time; $R^1$, $R^5$, $R^6$, and $R^7$ are each hydrogen or methyl; $R^2$ and $R^8$ are each no group, or each hydrogen or hydroxyl when there is no double bond at a and at f, respectively; $R^3$ is methylene when there is a double bond at b, or hydrogen or methyl when there is no double bond at b; $R^4$ is formyl or —$(CH_2)_n$—$R^{10}$, wherein $R^{10}$ is hydrogen, hydroxyl, acyloxy, or cyano and n is an integer of from 1 to 3; and $R^9$ is methylene when there is a double bond at g, or —$(CH_2)_n$—$R^{10}$ when there is no double bond at g.

6. The method according to claim 5, wherein the tyrosinase-inhibiting compound is selected from the group consisting of citronellol, geraniol, farnesol, nerolidol, dihydromyrcenol, citronellol, octanol, decanol, and the esters thereof derived from a carboxylic acid having one to four carbon atoms.

7. The method according to claim 6, wherein the tyrosinase-inhibiting compound is selected from the group consisting of citronellyl isobutyrate, geranyl isobutyrate, and farnesyl isobutyrate.

8. The method of claim 5, wherein the host has a tyrosinase-activity disorder.

\* \* \* \* \*